United States Patent [19]

Bui-Khac et al.

[11] Patent Number: 5,395,923

[45] Date of Patent: * Mar. 7, 1995

[54] PROCESS FOR THE OBTENTION OF A BIOLOGICAL ADHESIVE MADE OF CONCENTRATED COAGULATION FACTORS BY "SALTING-OUT"

[75] Inventors: Trung Bui-Khac, Montreal; Lise Lavoie, St-Eustache; Dominique Michel St Picq, Ste-Geneviéve, all of Canada

[73] Assignee: Haemacure-Biotech, Inc., Pointe-Claire, Canada

[ * ] Notice: The portion of the term of this patent subsequent to Mar. 1, 2011 has been disclaimed.

[21] Appl. No.: 21,302

[22] Filed: Feb. 23, 1993

[51] Int. Cl.$^6$ .............. C07K 3/24; C07K 15/06; A61K 37/02
[52] U.S. Cl. ............... 530/381; 530/382; 530/384; 530/419
[58] Field of Search ............... 530/381, 382, 384, 419; 424/89

[56] References Cited

U.S. PATENT DOCUMENTS

| | | | |
|---|---|---|---|
| 2,826,533 | 3/1958 | Fowell | 514/21 |
| 4,876,241 | 10/1989 | Feldman et al. | 514/2 |
| 4,877,608 | 10/1989 | Lee et al. | 424/85.8 |
| 5,030,215 | 7/1991 | Morse et al. | 604/410 |
| 5,290,918 | 3/1994 | Bui-Khai | 530/381 |

FOREIGN PATENT DOCUMENTS

| | | |
|---|---|---|
| 1128859 | 8/1982 | Canada . |
| 1245154 | 11/1988 | Canada . |
| 0305243 | 3/1989 | European Pat. Off. . |
| 3622642 | 1/1988 | Germany . |

OTHER PUBLICATIONS

Albert L. Lehninger "Biochemistry" 2nd ed. 1975 p. 162.

*Primary Examiner*—Jeffrey E. Russel
*Assistant Examiner*—Nancy J. Gromet
*Attorney, Agent, or Firm*—Merchant, Gould, Smith, Edell, Welter & Smith

[57] ABSTRACT

The present invention relates to a process of making a concentrate of coagulation proteins starting with whole human or animal plasma. This concentrate is used as a biological adhesive when extemporaneously mixed to thrombin. The concentrated proteins include mostly fibrinogen, fibrin stabilizing factor (factor XIII) and fibronectin. The claimed process has the advantage of being short of execution while providing an excellent yield of coagulable proteins. No protease inhibitor has to be added during the process. The process involves steps of separation by "salting-out" in presence of amino-6 hexanoic acid which prevents co-precipitation of plasminogen with the desired coagulable proteins. The proteins so obtained are very stable after reconstitution in water for at least 24 hours at room or body temperature. After mixing with thrombin and calcium, the adhesive shows excellent strength and biocompatibility.

16 Claims, No Drawings

PROCESS FOR THE OBTENTION OF A BIOLOGICAL ADHESIVE MADE OF CONCENTRATED COAGULATION FACTORS BY "SALTING-OUT"

FIELD OF THE INVENTION

Biological adhesives introduce a new approach to surgeries and sutures. Surgeons have sought for a long time an effective, easy-to-use and above all easily-tolerated adhesive that could be used in addition to or in replacement of sutures. Surgical sutures are important nowadays. However, numerous problems arise such as intolerance or toxicity.

The first tissue adhesive based on synthetic products appeared in the 60's; it was a adhesive of the cyanoacrylate family. It is a powerful adhesive, polymerized in a few seconds; but its use presents a considerable cellular toxicity. Other synthetic adhesives of the same family with longer radicals also possess haemostatic, bacteriostatic and healing properties, but they also show problems of inflammatory reactions and tissue toxicity still too considerable. In 1967, formaldehyde-based adhesives containing gelatin, resorcin and formalin were introduced. They brought certain improvement—less toxic than the preceding ones—but allergic reactions and tissue toxicity caused by formalin were recorded. Inflammatory reactions, tissue toxicity and allergies lead to the rejection of these not very biocompatible adhesives.

For these various reasons, research is under way to develop an adhesive combining the following properties:
Sufficient adhesivity
Good elasticity
Good hold on adjacent tissues
Absence of toxicity
Absence of metabolic action
Good tolerance Blood, through its coagulation properties, has always represented for surgeons an ideal model of biological gluing.

The adhesive power of blood clot, due to its network of polymerized fibrin, has been known for a long time. Fibrin has been used since the beginning of this century as an adhesive. In 1909, Bergel recognized it as a physiological gluing substance and moreover ascribed it healing properties. This discovery was immediately followed by Grey's work who used fibrin tampons to stop brain and liver haemorrhages. However, it is only in 1944 that Cronkite, then Tidrick and Warner used fibrinogen together with thrombin to secure skin graft. But the low concentration of these products did not allow a good quality adhesion nor a lasting effect. Since 1946, owing to important scientific research by E. J. Cohn on the fractionation of plasma proteins, coagulation proteins in particular have been used, and a few years later the mechanism of coagulation and main coagulation proteins, notably Factor XIII, were elucidated.

In 1975, Matras was the first to use fibrin adhesive properties through highly concentrated fibrinogen.

DESCRIPTION

The present invention consists in preparing a concentrate rich in fibrinogen and fibrin stabilizing factor (Factor XIII) either from human or animal whole plasma. This concentrate possesses all the necessary properties to lead to coagulation in presence of thrombin. The process described below is a method of preparation and use of this concentrate for therapeutic purposes.

Because of its coagulating properties, this concentrate provides clinicians with a precious and effective tool for surgery, where haemostatic properties are greatly needed. The fields of clinical applications may be: neurosurgery, cardiovascular surgery, plastic surgery (skin graft), ORL surgery, stomatology, orthopedic surgery, general surgery and traumatology.

The main protein in this concentrate is fibrinogen which through an enzymatic reaction in presence of thrombin and calcium ions produces fibrinopeptides A and B permitting the formation of fibrin monomers. These monomers polymerize quickly and become soluble fibrin. Then, the fibrin stabilizing factor under the agency of calcium ions forms covalent bonds with the dissolved fibrin which make it stable and insoluble in an acid medium or in presence of urea.

The fibrin thus formed is irreversible, stable and fully plays its role as coagulant. It resists fibrinolysis because of its high concentration, and keeps its shape as a result of the absence of exudation. This concentrate has the following characteristics: excellent stability after being dissolved again in an aqueous solution, solubilization at room temperature in a few minutes, good elasticity and, lastly, a good adhesion.

These characteristics depend only on the method of preparation from plasma. This is a simple, quick method easily adaptable to industrial production. All the concentrate biological and biochemical properties are preserved, and the product meets clinicians' requirements.

There already are biological adhesives described in Canadian patent No 1,128,859 and No 1,245,154 that contain fibrinogen and factor XIII. These adhesives are made from a plasma cryoprecipitate at $+2°$ C. This cryoprecipitate is then treated with a buffer containing a plasminogen activator-inhibitor or a plasmin inhibitor which remain in the end product. These products show interesting characteristics. But their method of production is rather complex and requires adjunction of inhibitors, such as protease inhibitors from animal sources, aprotinin for instance, and plasma proteins from human source, albumin for example, during preparation.

Moreover, the products prepared according to these above-mentioned patents are soluble neither in aqueous solution, nor at room temperature. They are soluble at $37°$ C. under mechanical agitation with a bar magnet introduced in the flask before lyophilisation. However, in spite of the high temperature and extra equipment, these products take more than 30 minutes to give a homogenous solution.

Another method of preparation for biological adhesive is described in the European patent No 0,305,243 B1. It is prepared by precipitation of coagulation proteins in diluted ethyl alcohol starting with whole plasma. This product has much better characteristics than the preceding ones. This product is put back in solution at room temperature in less than 10 minutes, which meets one the clinicians' requirements. In spite of this advantage, the preparation of the product seems too long because the introduction of ethanol in the plasma leads to a settling period of 12 to 24 hours for the proteins. This hinders processing on a continuous basis which is often expected in the industry. A third method of preparation of biological adhesive developed in Germany is described in patent No DE 3,622,642 A1. This adhesive similar to those described in the above-mentioned patents has the advantage of being quickly solubilized in aqueous solution at room temperature, but its mode of preparation still involves the adjunction of protease inhibitors, albumin, prothrombin and antithrombin.

According to the present invention, the concentrate must be subjected to virus inactivation by mixing with a solvent and a detergent to destroy pathogenic viruses such as hepatitis and AIDS virus. The end product obtained by the described method undergoes no modification in its structure or biological activity. These product characteristics are related to its performance in solubilization and stability which gives it a wide range of uses.

The concentrate solubilizes in less than 10 minutes, at room temperature without any special equipment. It is stable for several hours after its dissolution.

The inventor has also developed a process both original and very simple to obtain a protein concentrate coagulable in presence of thrombin simply through a cold "salting out" step at a slightly basic pH.

The method yields more than 85% of coagulable fibrinogen out of the total protein present in the concentrate, an important quantity of fibrin stabilization factor (Factor XIII), a satisfactory amount of fibronectin, and most of all, it allows elimination of plasminogen, a pro-enzyme known for its fibrinolytic properties. Plasminogen, if present, would produce a deleterious effect on the product.

The invention consists in preparing a concentrate rich in proteins coagulable by thrombin. This concentrate is obtained by precipitation with a salt (for example, an acetate salt) starting with human or animal plasma. The precipitate contains more than 85% by weight of coagulable fibrinogen as well as Factor XIII which is precipitated along with the fibrinogen. This Factor XIII is present at a concentration of at least 300 to 400 IU per gram of protein (or 300–350 IU/g fibrinogen). This concentrate, contrarily to those currently commercialised, solubilizes quickly in an aqueous solution at room temperature in less than 10 minutes and has a protein content of up to 150 mg/ml. Moreover, it remains stable for at least 24 hours after its reconstitution at a temperature between 4° to 37° C. The concentrate also contains a balanced quantity of fibronectin in the range of 0.06±0.02 g per gram of protein. The concentrate, according to the invention, is obtained by a method comprising a step of precipitation of whole plasma by a salt at a sufficient concentration to achieve the salting-out process at a pH comprised between 7.50 and 8.50, in presence of amino-6 hexanoic acid and a temperature comprised between 0° and 4° C. No particular precautions are necessary, coagulable proteins precipitate quickly and completely and not after many hours or even several days as is the case in existing patents. The addition of amino-6 hexanoic acid abolishes the affinity of plasminogen toward fibrinogen and renders there two proteins easily separable.

This method is adaptable to industrial production with a considerable time saving and to continuous processing. The whole plasma is contacted with the salt at a minimum concentration of about 0.5M per liter of plasma in presence of a minimal concentration of 50 mM amino-6 hexanoic acid. Coagulable proteins precipitate, under agitation, in a few minutes. The duration of the precipitation should ideally be of at least 30 minutes for allowing maximal recovery. The remaining solution is separated by centrifugation and may be used to prepare other plasma proteins.

After centrifugation, the precipitate is put back into solution in a Tris-sodium citrate buffer. The protein concentration is then about 20 to 30 mg per ml of solution. The pH is adjusted by the addition of L-histidine. This solution is then subjected to a process aimed at the inactivation of pathogen virus such as those of AIDS and hepatitis, such a process being described in U.S. Pat. Nos. 4,540,573, 4,764,363 and 4,820,805. This consists in a solvent-detergent treatment at 28° C. during 6 hours under gentle agitation. The protein content is then between 10 to 15 mg/ml. The organic products used to inactivate the viruses are separated during protein precipitation by salts and amino-6 hexanoic acid. They are then eliminated by centrifugation, the supernatant solution containing organic products as well as contaminating proteins such as albumin and immunoglobulins. The precipitate obtained after this step is wash thoroughly with slightly acidic pure water.

The washings also eliminate residual chemicals, contaminating proteins and salts such as citrate which adversely affect coagulation efficiency.

The final precipitate is put back into solution in a buffer containing Tris and L-Histidine. Finally, the protein solution is filtered, then sterilized by filtration. The sterile solution is put into flasks under conditions of absolute sterility. These flasks are subjected to a 48-hour lyophilization.

The following examples more readily describe the process for the preparation of the concentrate according to the invention.

EXAMPLE 1

Fresh plasma frozen to below −35° C. is defrosted quickly at 37° C., and then incubated at this temperature for at least fifteen minutes in presence of a minimal concentration of 50 mM of amino-6 hexanoic acid, and then cooled to between 0°–4° C. Sodium or potassium acetate is added to the previously cooled plasma at the rate of one mole per liter of plasma. This is continuously agitated for one hour between 0°–4° C. and centrifuged at 3700 RPM (JS 4.2 rotor type; Beckman J6-MC centrifuge) at 4° C. during 20 minutes. The precipitate obtained, rich in fibrinogen and Factor XIII, is transferred to a vessel containing a 1% Tris solution and 1.6% of sodium citrate pH 7.30. The precipitate is solubilized at room temperature, under magnetic agitation. The buffer described above is added as needed to get a protein concentration of about 20–22 mg/ml. At this point, L-Histidine is added at the rate of 0.2–0.3 g per gram of protein. The protein solution is then passed through filters with a porosity of 0.8 micron. The solution thus filtered is subjected to a virus inactivation treatment by mixing with an equal volume of a solution containing 1% Tris, 1.6% sodium citrate (pH 7.3), 2% Tween 80 ® and 0.6% Tri-n-butyl-phosphate (TNBP).

This brings the final concentration to about 10 mg/ml proteins, 1% Tween 80 and 0.3% TNBP. The solution is incubated at 28° C., under constant agitation for a six-hour period. After the virus inactivation treatment, the protein solution is cooled between 0°–4° C., and then, under minimal agitation, 50 mM amino-6 hexanoic acid is added. A quantity of acetate equivalent to one mole is added, and the precipitate appears instantaneously.

Agitation continues for one hour at between 0°–4° C. The solvent, the detergent and the contaminating proteins are eliminated by centrifugation. The precipitate is recovered and washed several times with a 0.1% Tris solution (pH 4.50–5.0) until a neutral pH is reached. The number of washing steps may be decreased by performing a simple dialysis or a diafiltration after the precipitate is put back into solution in 0.5% Tris (pH 7.30).

The washed precipitate is dissolved in a 0.5% Tris solution. After complete solubilization, the solution pH and osmolarity are adjusted. The pH is brought to 7.30–7.50. The final protein concentration is around 30 to 35 mg/ml of solution. A quantity of L-Histidine corresponding to 0.2–0.3 g per gram of proteins is added and a quantity of saccharose equivalent to 50% (w/w) with respect to protein. The final protein solution is filtered and packaged under sterile conditions; it is then lyophilised for 48 hours.

EXAMPLE 2

The lyophilised product obtained by this method has been reconstituted with one ml for each vial distilled water and analyzed biochemically.

The results of these analyses make it possible to determine the composition and the quality of the concentrate according to the present invention as a biological adhesive.

A.—Biochemical Analysis (Example 1):

The concentrate protein content is as follows:

| | |
|---|---|
| Coagulable fibrinogen (measured by gravimetry): | 95–105 mg/ml |
| Factor XIII endogenous: | 35–40 UI/ml |
| Fibronectin: | 4–6 mg/ml |
| Plasminogen: | 0.010–0.015 mg/ml |
| Albumin: | 0.10–0.20 mg/ml |
| Immunoglobulins: | |
| Ig A: | 0.20–0.30 mg/ml |
| Ig G: | 0.50–0.60 mg/ml |
| Ig M: | 0.20–0.30 mg/ml |

As mentioned above, the concentrate prepared according to the present invention is characterized by its excellent solubilization and stability. It is put back in solution in less than five minutes at room temperature (20°–25° C.) with only manual agitation. We chose to use pure water as a solvent for our product because it presents obvious advantages for our biochemical analysis. Nevertheless, like the other currently commercialized products, the instant concentrate should be reconstituted in a solution of aprotinin to avoid fibrinolysis when in contact with body parts, such fibrinolysis compromising the stability of the adhesive.

We have noticed no degradation or destabilization of the product reconstituted in pure water at 4° C. or 20° C. for a period that could extend over 24 hours, suggesting that the concentrate is protease free.

After reconstitution in water, the fibrinogen is mixed to a solution of thrombin in presence of calcium chloride. The fibrin thus formed is totally free from exudation.

B.—Strength analysis:

The adhesive power determined on animals by gluing mice pieces of skin, is superior to 200 g/cm³. This adhesive power has also been shown by gluing two pieces of gauze; this test is described on the sketch below. The product is perfectly stable for 24 hours at a holding temperature of 4° or 20° C. The adhesive power determined by this technique is 350±20 g/cm³ after 10 minutes of contact, under a pressure of one kg, for a mixture of 0.050 ml of protein solution, 0.050 ml bovine thrombin (100 IU/ml in 40 mM of calcium chloride). A test after a 24-hour holding period shows that the adhesive power remains unchanged.

C.—Evaluation of biocompatibility:

The evaluation of the biocompatibility of the instant adhesive was conducted in vitro using cultured cells. This evaluation was directed toward cytotoxicity and cytocompatibility (cellular proliferation, DNA synthesis, etc.).

The cultured cells tests were Balb 3T3 cells and/or human skin fibroblasts. The cytotoxicity was measured by the incorporation of neutral red. When alive, the cells are impregnated with this dye which is fixed to cell liposomes. When dead, the cells do not take up the dye. Dosing of the dye is done after 72 hours of contact with the cells. The evaluation of the viability of the cells can also be done by microscopic observation (under Canadian standard CAN 3-Z310.6-M 84) or by cell counts.

The adhesive is not cytotoxic under the described conditions. It has an increasing effect on cellular density (45% for fibroblasts and 124% for Balb 3T3 cells).

Quick solubilization, great stability in solution and absence of exudation are the main characteristics of the concentrate according to the present invention.

These characteristics confer it great flexibility: time saving, quick dissolution, variable temperatures and use over a prolonged period. These performances show the product adaptability to constraints faced by surgeons in operation rooms.

These concentrates of protein rich in fibrinogen and Factor XIII prepared for therapeutic use according to the present invention may be obtained from human or animal plasma and therefore be useable either in medical or veterinary practices.

What is claimed is:

1. A method for the preparation of a protein concentrate coagulable by thrombin, which protein concentrate consists essentially of fibrinogen, endogenous Factor XIII and fibronectin, characterized in that it comprises the following steps:

(a) a first precipitation effected on whole plasma proteins by the addition of a salt in a sufficient quantity to achieve a salting out effect and a pH of 7.5 to 8.5, whereby fibrinogen, Factor XIII and fibronectin are selectively precipitated to provide precipitated proteins, said selective precipitation being conducted at 0° to 4° C., in the presence of a concentration of at least 50 mM of amino-6 hexanoic acid;

(b) a first solubilization of the precipitated proteins in the presence of 0.2 to 0.3 g of L-Histidine per gram of proteins to form a solution containing the proteins;

(c) a viral deactivation step of the solution obtained in step (b) in a solvent-detergent solution;

(d) a second precipitation by the same salt as in step (a) at the same temperature, in the presence of the same concentration of amino-6 hexanoic acid to form a second precipitate;

(e) a washing of the second precipitate to bring the washed second precipitate to a neutral pH;

(f) a second solubilization of the washed second precipitate in the presence of 0.2 to 0.3 g of L-Histidine per gram of proteins;

(g) an addition of 50% saccharose with respect to the quantity of proteins obtained by step (f) to form a solution;

(h) a sterile filtration of the solution obtained in step (g) to form a filtered solution;

(i) an aliquoting of the filtered solution of step (h) in sterile bottles; and (j) a lyophilisation of the solution aliquoted in step (i) to provide a lyophilized concentrate.

2. A method according to claim 1, characterized in that said salt is sodium or potassium acetate.

3. A method according to claim 1 characterized in that said first and second precipitation steps are conducted for a period of time of at least 30 minutes.

4. A method according to claim 1, characterized in that step (e) is performed at 2° C.

5. A method according to claim 1, characterized in that each of steps (a), (d) and (e) is performed for at least 30 minutes.

6. A method according to claim 1, characterized in that step (e) further comprises (i) solubilizing the second washed precipitate in pure water basified to a pH of about 7.3; and (ii) dialyzing or diafiltering the solubilized second precipitate of step (i);

and step (f) further comprises adding the L-Histidine to the dialyzed or diafiltered precipitate to a final concentration of 0.2 to 0.3 g of L-Histidine per gram of proteins.

7. A method according to claim 1, characterized in that the second precipitate is washed with a solution of Tris-HCl 0.1% of pH 4.5–5.0 made in pure water.

8. A method according to claim 6, characterized in that said basified pure water used for solubilizing the second precipitate before dialysis or diafiltration is a solution of Tris 0.5% made in pure water.

9. A method according to claim 1 characterized in that said first solubilization is made in 1% Tris and 1.6% sodium citrate pH 7.30 to bring the protein concentration to 20–22 mg/mL before adding L-Histidine.

10. A method according to claim 1 characterized in that said second solubilization is made in Tris 0.5% pH 7.30 to bring the protein concentration to 30–35 mg/mL before adding L-Histidine.

11. A method according to claim 1 characterized in that said viral deactivation is performed at 28° C. during six hours under continuous agitation in a solution consisting of 10 mg/mL of solubilized proteins, 1% Tween 80 ® and 0.3% Tri-n-butyl-phosphate.

12. A method according to claim 1, characterized in that the lyophilized concentrate solubilizes in water in less than five minutes at room temperature under manual agitation to form a solubilized concentrate.

13. A method according to claim 12 characterized in that the solubilized concentrate is stable at a temperature of 4°–20° C. for at least 24 hours.

14. A method according to claim 1, wherein said whole plasma proteins are of human or of animal origin.

15. A method according to claim 1, characterized in that said lyophilized concentrate of step (j) solubilizes and remains stable in water for at least 24 hours at room temperature.

16. A method according to claim 1, characterized in that step (e) is performed at room temperature.

* * * * *

UNITED STATES PATENT AND TRADEMARK OFFICE
CERTIFICATE OF CORRECTION

PATENT NO.    :    5,395,923
DATED         :    Mar. 7, 1995
INVENTOR(S)   :    Bui-Khac et al.

It is certified that error appears in the above-identified patent and that said Letters Patent is hereby corrected as shown below:

On the cover page, under [56] References Cited, for "Bui-Khai" read --Bui-Khac--.

At column 5, at lines 61 and 66, for "g/cm$^3$" read --g/cm$^2$--.

Signed and Sealed this

Nineteenth Day of September, 1995

Attest:

BRUCE LEHMAN

*Attesting Officer*    *Commissioner of Patents and Trademarks*